United States Patent
Xuan et al.

(10) Patent No.: US 12,203,109 B2
(45) Date of Patent: *Jan. 21, 2025

(54) PHOSPHOLIPASE C MUTANT WITH HIGH ENZYME ACTIVITY

(71) Applicant: Wilmar (Shanghai) Biotechnology Research & Development Center Co., Ltd, Shanghai (CN)

(72) Inventors: Yaoji Xuan, Shanghai (CN); Qiwen Niu, Shanghai (CN); Zhengjun Xu, Shanghai (CN)

(73) Assignee: Wilmar (Shanghai) Biotechnology Research & Development Center Co., Ltd, Shanghai (CN)

( * ) Notice: Subject to any disclaimer, the term of this patent is extended or adjusted under 35 U.S.C. 154(b) by 642 days.

This patent is subject to a terminal disclaimer.

(21) Appl. No.: 17/419,091

(22) PCT Filed: Dec. 27, 2019

(86) PCT No.: PCT/CN2019/128970
§ 371 (c)(1),
(2) Date: Jun. 28, 2021

(87) PCT Pub. No.: WO2020/135657
PCT Pub. Date: Jul. 2, 2020

(65) Prior Publication Data
US 2022/0064611 A1   Mar. 3, 2022

(30) Foreign Application Priority Data
Dec. 28, 2018  (CN) .......................... 201811620055.7

(51) Int. Cl.
| | | |
|---|---|---|
| C12N 9/16 | (2006.01) | |
| C11B 3/00 | (2006.01) | |
| C12N 1/14 | (2006.01) | |
| C12N 15/81 | (2006.01) | |
| C12R 1/84 | (2006.01) | |

(52) U.S. Cl.
CPC ............... *C12N 9/16* (2013.01); *C11B 3/003* (2013.01); *C12N 1/14* (2013.01); *C12N 15/815* (2013.01); *C12R 2001/84* (2021.05); *C12Y 301/04003* (2013.01)

(58) Field of Classification Search
None
See application file for complete search history.

(56) References Cited

U.S. PATENT DOCUMENTS

2013/0011887 A1  1/2013 Dayton et al.
2017/0058235 A1  3/2017 Damstrup et al.

FOREIGN PATENT DOCUMENTS

| CN | 104630174 A | 5/2015 |
|---|---|---|
| CN | 106459935 A | 2/2017 |
| CN | 106884009 A | 6/2017 |
| CN | 108384768 A | 8/2018 |
| WO | 2015140275 A1 | 9/2015 |

OTHER PUBLICATIONS

Ngo et al. in the Protein Folding Problem and Tertiary Structure Prediction, 1994, Merz et al. (ed.), Birkhauser, Boston, MA, pp. 433 and 492-495.*
Guo et al., PNAS, vol. 101, No. 25, pp. 9205-9210, Jun. 2004.*
Durban et al., High Level Expression of a Recombinant Phospholipase C from Bacillus Cereus in Bacillus Subtilis, Applied Microbiology and Biotechnology, 2007, 74(3):634-639.
Hough et al., High-Resolution (1.5 Å) Crystal Structure of Phospholipase C from Bacillus Cereus, Nature, 1989, 338(6213):357-360.
Johansen et al., Cloning and Sequencing of the Gene Encoding the Phosphatidylcholine-Preferring Phospholipase C of Bacillus Cereus, Gene, 1988, 65(2):293-304.
NCBI Reference Sequence: WP_048557546.1, Phospholipase C [Bacillus Cereus], https://www.ncbi.nlm.nih.gov/protein/WP_048557546.1, Jul. 10, 2019, 1 page.
Needleman et al., A General Method Applicable to the Search for Similarities in the Amino Acid Sequence of Two Proteins, Journal of Molecular Biology, 1970, 48:443-453.
Rice et al., EMBOSS: The European Molecular Biology Open Software Suite, Trends in Genetics, 2000, 16(6):276-277.
Romanos et al., Foreign Gene Expression in Yeast: A Review, Yeast, 1992, 8:423-488.
Sambrook et al., Molecular Cloning, A Laboratory Manual, Second Edition, Cold Spring Harbor Laboratory Press 1989.
Seo et al., High-Level Expression of Recombinant Phospholipase C from Bacillus Cereus in Pichia Pastoris and its Characterization, Biotechnology Letters, 2004, 26(19):1475-1479.
PCT International Search Report and Written Opinion, PCT/CN2019/128970, Mar. 24, 2020, 13 pages.
European Patent Office, Extended European Search Report, Application No. 19902338.3, Sep. 15, 2022, 8 pages.

* cited by examiner

Primary Examiner — Richard G Hutson
(74) Attorney, Agent, or Firm — Quarles & Brady LLP (57) ABSTRACT

Provided in the present invention is a phospholipase C mutant with high enzyme activity, a polypeptide with the sequence as shown in SEQ ID NO:7, or a polypeptide derived from the phospholipase C formed by performing substitution, deletion or addition of one or a plurality of amino acids on the polypeptide of SEQ ID NO:7 while retaining the phospholipase C activity provided by SEQ ID NO:7. The phospholipase C mutant of the present invention can improve degumming efficiency and increase the yield of diacylglycerol (DAG) during degumming.

17 Claims, 1 Drawing Sheet
Specification includes a Sequence Listing.

SEQUENCE LISTING

```
<160> NUMBER OF SEQ ID NOS: 7

<210> SEQ ID NO 1
<211> LENGTH: 738
<212> TYPE: DNA
<213> ORGANISM: Artificial Sequence
<220> FEATURE:
<223> OTHER INFORMATION: DNA sequecne of PLC-N63DN131SN134D-Y56H

<400> SEQUENCE: 1
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgatcatga aaacccctat     180
tacgatgaca gtaccttcgc ttctcacttt tacgatccag acaacggaaa gacatatatc     240
ccattcgcca agcaagctaa ggagactgga gctaagtact tcaagttggc tggagagtca     300
tacaagaata aagacatgaa gcaggccttc ttttatcttg ggttgtcatt gcattatttg     360
ggcgatgtca accaacctat gcatgccgca tcctttacgg acctgtccta tccacagggt     420
tttcactcca agtacgagaa ctttgtcgat actattaaag acaactacaa agttaccgat     480
gggaacggat attggaattg gaaaggcacc aaccctgaag aatggattca cggtgcagca     540
gtagttgcaa aacaggacta ctctggaatt gtcaatgaca ataccaaaga ttggtttgtg     600
aaagccgcag tctcccagga atatgcagat aaatggagag ctgaagttac acctatgact     660
ggtaaacgac taatggatgc ccaaagagtt actgctggtt acattcaatt atggttcgac     720
acttacggtg acaggtaa                                                   738

<210> SEQ ID NO 2
<211> LENGTH: 245
<212> TYPE: PRT
<213> ORGANISM: Artificial Sequence
<220> FEATURE:
<223> OTHER INFORMATION: amino acid sequecne of PLC-N63DN131SN134D-Y56H
```

<400> SEQUENCE: 2

Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp His Glu Asn Pro Tyr Tyr Asp Asp Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Ser Phe Thr Asp Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Val Ser Gln Glu Tyr
    195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
            245

<210> SEQ ID NO 3
<211> LENGTH: 738
<212> TYPE: DNA
<213> ORGANISM: Artificial Sequence
<220> FEATURE:
<223> OTHER INFORMATION: coding sequence of mutant

<400> SEQUENCE: 3

```
tggtcagctg aggacccgca tgttgaatcg gtgaatagtc acttatggat cgtgaaccgt    60
gccattgata taatgtctag gaatacaact ctggttaagc aagatagagt tgctcaattg   120
aatgaatggc gtacagagct agagaatggc atctacgctg ctgatcatga aaaccccta    180
tacgatgaca gtaccttcgc ttctcacttt tacgatccag acaacggaaa gacatatatc   240
ccattcgcca agcaagctaa ggagactgga gctaagtact tcaagttggc tggagagtca   300
tacaagaatt ctgacatgaa gcaggccttc ttttatcttg gttgtcatt gcattatttg    360
ggcgatgtca accaacctat gcatgccgca tcctttacgg acctgtccta tccacagggt   420
tttcactcca gtacgagaa ctttgtcgat actattaaag acaactacaa agttaccgat   480
gggaacggat attggaattg gaaaggcacc aaccctgaag aatggattca cggtgcagca   540
gtagttgcaa acaggacta ctctggaatt gtcaatgaca ataccaaaga ttggtttgtg   600
```

```
aaagccgcag tctcccagga atatgcagat aaatggagag ctgaagttac acctatgact    660
ggtaaacgac taatggatgc ccaaagagtt actgctggtt acattcaatt atggttcgac    720
acttacggtg acaggtaa                                                  738
```

```
<210> SEQ ID NO 4
<211> LENGTH: 245
<212> TYPE: PRT
<213> ORGANISM: Artificial Sequence
<220> FEATURE:
<223> OTHER INFORMATION: amino acid sequecne of mutant

<400> SEQUENCE: 4
```

Trp Ser Ala Glu Asp Pro His Val Glu Ser Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp His Glu Asn Pro Tyr Tyr Asp Asp Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Ser Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Ser Phe Thr Asp Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245

```
<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
```

```
cgactggttc caattgacaa cg                                              22
```

```
<210> SEQ ID NO 6
```

```
<211> LENGTH: 24
<212> TYPE: DNA
<213> ORGANISM: Artificial Sequence
<220> FEATURE:
<223> OTHER INFORMATION: primer

<400> SEQUENCE: 6
ggcaaatggc attctgacat cctc                                              24

<210> SEQ ID NO 7
<211> LENGTH: 245
<212> TYPE: PRT
<213> ORGANISM: Artificial Sequence
<220> FEATURE:
<223> OTHER INFORMATION: amino acid sequecne of mutant
<220> FEATURE:
<221> NAME/KEY: MUTAGEN
<222> LOCATION: (6)..(6)
<223> OTHER INFORMATION: Xaa is alanine, valine, leucine, isoleucine,
      proline, phenylalanine, methionine or tryptophan
<220> FEATURE:
<221> NAME/KEY: MUTAGEN
<222> LOCATION: (8)..(8)
<223> OTHER INFORMATION: Xaa is alanine, valine, leucine, isoleucine,
      proline, phenylalanine, methionine or tryptophan
<220> FEATURE:
<221> NAME/KEY: MUTAGEN
<222> LOCATION: (10)..(10)
<223> OTHER INFORMATION: Xaa is Glycine, asparagine, glutamine, serine,
      threonine, tyrosine or cysteine
<220> FEATURE:
<221> NAME/KEY: MUTAGEN
<222> LOCATION: (104)..(104)
<223> OTHER INFORMATION: Xaa is Glycine, asparagine, glutamine, serine,
      threonine, tyrosine or cysteine

<400> SEQUENCE: 7
```

Trp Ser Ala Glu Asp Xaa His Xaa Glu Xaa Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp His Glu Asn Pro Tyr Tyr Asp Asp Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Xaa Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Ser Phe Thr Asp Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

-continued

```
Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245
```

PHOSPHOLIPASE C MUTANT WITH HIGH ENZYME ACTIVITY

CROSS-REFERENCE TO RELATED APPLICATIONS

This application represents the U.S. national stage entry of International Application No. PCT/CN2019/128970 filed Dec. 27, 2019, which claims priority to Chinese Patent Application No. 201811620055.7 filed Dec. 28, 2018, the disclosure of which is incorporated herein by reference in its entirety and for all purposes.

REFERENCE TO A SEQUENCE LISTING SUBMITTED VIA EFS-WEB

The content of the ASCII text file of the sequence listing named "850766-00114-ST25.txt" which is 9.94 KB in size was created on Jun. 28, 2021 and electronically submitted via EFS-Web herewith, the application is incorporated herein by reference in its entirety.

FIELD OF DISCLOSURE

The disclosure relates to a phospholipase C mutant with high enzyme activity.

BACKGROUND OF DISCLOSURE

Degumming is an important step in oil and fat refining. The traditional hydration degumming method suffers from high cost, high material and energy consumption and serious environmental pollution. Therefore, recently many efforts have been devoted to the use of enzymatic degumming in the degumming process of oil and fat refining, and great progress has been made. Compared with traditional methods, enzymatic degumming can improve economic benefits, save energy, reduce emission, decrease environmental pollution, thus has greater advantages in environmental protection, economy, and quality. The enzyme used in oil and fat degumming is phospholipase. As compared with other degumming enzymes, phospholipase C (PLC) shows greater advantages, such as increased yield of diacylglycerol (DAG) and reduced loss of oil yield.

PC-PLC from *Bacillus cereus* (BC-PC-PLC) is a phospholipase C that has been studied earlier. BC-PC-PLC has a full length of 283 amino acids, including a signal peptide of 24 amino acids and a leader peptide of 14 amino acids. The mature peptide of BC-PC-PLC has 245 amino acids (Johansen et al. 1988). It is reported that the crystal structure of BC-PC-PLC consists of multiple helical domains with a catalytic site of D55, and at least three Zn2+ binding sites (Hough et al. 1989). Little has been studied about the heterologous expression of BC-PC-PLC other than that in *Bacillus subtilis* and *Pichia pastoris* (Durban et al. 2007; Seo et al. 2004).

In previous studies, the inventors have obtained a mutant with greatly improved specific enzyme activity as compared to wild type by mutation of N56, N63, N131 and N134 of BC-PC-PLC to H, D, S and D, respectively. In order to further improve the specific enzyme activity and degumming efficiency of the phospholipase C, the inventors selected amino acids 6, 8, 10, 104, and 205 of BC-PC-PLC for random saturation mutagenesis By directed evolution of the existing phospholipase C mutant, it is hoped that the specific enzyme activity can be further improved, so as to obtain more efficient phospholipase C, improve the degumming efficiency, and increase the diacylglycerol (DAG) yield during the degumming process.

SUMMARY OF DISCLOSURE

The disclosure provides an isolated polypeptide selected from the group consisting of:
(1) a polypeptide shown by SEQ ID NO: 7; and
(2) a polypeptide having at least 80%, preferably at least 85%, more preferably at least 90%, more preferably at least 95%, more preferably at least 97%, more preferably at least 98%, more preferably at least 99% sequence identity to SEQ ID NO:7, wherein the amino acid residues of the polypeptide that correspond to at least one of amino acids 6, 8, 10 and 104 of SEQ ID NO: 7 are the same as amino acids 6, 8, 10 and/or 104 of SEQ ID NO: 7, respectively, and the polypeptide has phospholipase C activity of SEQ ID NO: 7.

In one or more embodiments, amino acid 6 of SEQ ID NO: 7 is proline or tryptophan; amino acid 8 is alanine, leucine or isoleucine; amino acids 10 and 104 are each independently serine or threonine.

In one or more embodiments, the isolated polypeptide is as shown in SEQ ID NO: 4.

The disclosure further provides an isolated polypeptide having at least 80%, preferably at least 85%, more preferably at least 90%, more preferably at least 95%, more preferably at least 97%, more preferably at least 98%, more preferably at least 99% sequence identity to SEQ ID NO:4, wherein the amino acid residues of the isolated polypeptide that correspond to amino acids 6, 8, 10 and 104 of SEQ ID NO: 4 are proline, valine, serine and serine, respectively; preferably, the polypeptide is obtained from *Bacillus subtilis*.

The disclosure also provides a polynucleotide sequence selected from the group consisting of:
(1) a polynucleotide sequence encoding a polypeptide according to any of the embodiments herein; and
(2) a complementary sequence of the polynucleotide sequence of (1); and
(3) a 15 to 30 bp fragment of the sequence of (1) or (2); preferably, the polynucleotide sequence is as shown in SEQ ID NO: 3.

The disclosure also provides a nucleic acid construct comprising a polynucleotide sequence according to any of the embodiments herein and one or more regulatory sequences operably linked to the polynucleotide sequence.

In one or more embodiments, the nucleic acid construct is a vector.

In one or more embodiments, the vector is an expression vector or a cloning vector.

The disclosure also provides a genetically engineered host cell, which contains a polynucleotide sequence or nucleic acid construct according to any of the embodiments herein.

The disclosure also provides a composition containing a polypeptide according to any of the embodiments herein and optionally adjuvants, preferably, the adjuvants are adsorption materials selected from the group consisting of: activated carbon, alumina, diatomaceous earth, porous ceramics, and porous glass.

The disclosure also provides use of a polypeptide, polynucleotide sequence, nucleic acid construct, host cell or composition according to any of the embodiments herein in oil and fat refining, phospholipid modification, feed modifier, food industry and pharmaceutical industry.

The disclosure also provides an enzymatic degumming method, comprising degumming using a polypeptide according to any of the embodiments herein; preferably, the method includes a step of contacting the polypeptide with crude oil; preferably, the step includes contacting the polypeptide with crude oil of 50 to 70° C.

In one or more embodiments, the method comprises one or more of the following features:
(1) based on the weight of the crude oil, the polypeptide is added in an amount of 10 to 1000 ppm, preferably 50 to 500 ppm, more preferably 100 to 300 ppm;
(2) the degumming includes: stirring at 50 to 60° C. for 1 to 3 hours, and then raising the temperature to 80 to 90° C. and holding for 1 to 10 minutes; and
(3) the crude oil is selected from the group consisting of: soybean oil, sunflower oil, peanut oil, rapeseed oil, rice bran oil, corn oil, olive oil, palm oil, palm kernel oil, palm olein, canola oil, castor oil, coconut oil, coriander oil, cottonseed oil, hazelnut oil, hempseed oil, linseed oil, mango kernel oil, meadowfoam oil, neat's foot oil, safflower oil, camellia oil, tall oil, and tsubaki oil.

DETAILED DESCRIPTION

It should be understood that, within the scope of the disclosure, the above technical features of the disclosure and the technical features specifically described in the following (e.g., Examples) can be combined with each other, thereby forming preferred technical solution(s).

The disclosure provides an isolated polypeptide of the amino acid sequence shown in SEQ ID NO: 7, or an isolated polypeptide having at least 80%, preferably at least 85%, more preferably at least 90%, more preferably at least 95%, more preferably at least 97%, more preferably at least 98%, more preferably at least 99% sequence identity to SEQ ID NO:7, wherein the amino acid residues of the polypeptide that correspond to at least one of amino acids 6, 8, 10 and 104 of SEQ ID NO: 7 are the same as amino acids 6, 8, 10 and/or 104 of SEQ ID NO: 7, respectively, and the polypeptide has phospholipase C activity of SEQ ID NO: 7.

Herein, "isolated" means a form or substance that does not exist in nature. Non-limiting examples of isolated substances include any non-naturally occurring substance and any substance that is at least partially removed from one or more or all of naturally occurring components associated with it in nature, including but not limited to any enzyme, variant, nucleic acid, protein, peptide or cofactor. For SEQ ID NO: 7, the amino acid residues (Xaa) at positions 6 and 8 can be amino acid residues having non-polar side chain, including but not limited to alanine, valine, leucine, isoleucine, proline, phenylalanine, methionine, and tryptophan; the amino acid residues (Xaa) at positions 10 and 104 can be amino acids having uncharged polar side chain, including but not limited to glycine, asparagine, glutamine, serine, threonine, tyrosine, or cysteine. Preferably, amino acid 6 of SEQ ID NO: 7 is proline or tryptophan; amino acid 8 is alanine, leucine or isoleucine; amino acids 10 and 104 are each independently serine or threonine. The amino acid sequence of an exemplary polypeptide is shown in SEQ ID NO: 4.

The disclosure also includes polypeptides having one or more (usually 1 to 10, such as 1, 2, 3, 4, 5, 6, 7, 8, 9 or 10) amino acid mutations (deletion, insertion and/or substitution) based on SEQ ID NO: 7, while retaining the phospholipase C activity of the amino acid sequence shown in SEQ ID NO: 4. In some embodiments, the amino acid mutation is the addition of one or several (usually within 20, preferably within 10, more preferably within 8) amino acids at the C-terminal and/or N-terminal of SEQ ID NO: 7. It should be understood that the one or more amino acid mutations generally do not include the case where all the amino acids (Xaa) at positions 6, 8, 10 and 104 of SEQ ID NO: 7 are mutated.

The mutation is preferably a conservative substitution. For example, in the art, conservative substitution using amino acids with close or similar properties typically does not change the function of the polypeptide or protein. The term "amino acids with close or similar properties" includes, for example, a family of amino acids having similar side chains. These families include amino acids with basic side chain (e.g., lysine, arginine, histidine), amino acids with acidic side chain (e.g., aspartate, glutamate), amino acids with uncharged polar side chain (e.g., glycine, asparagine, glutamine, serine, threonine, tyrosine, cysteine), amino acids with non-polar side chain (e.g., alanine, valine, leucine, isoleucine, proline, phenylalanine, methionine, tryptophan), amino acids with β-branched side chain (e.g., threonine, valine, isoleucine), and amino acids with aromatic side chain (e.g., tyrosine, phenylalanine, tryptophan, histidine). Therefore, replacing one or several amino acid residues in the polypeptide of the disclosure with another amino acid residue from a family of amino acids of the same side-chain class will not substantially affect the polypeptide's activity.

In the disclosure, the term "random saturation mutagenesis" refers to the process of using NNK degenerate codons in PCR primers for the site to be mutated, which can cover all 20 amino acids to achieve saturation mutagenesis Meanwhile, because multiple sites are selected for the mutagenesis the combination is random. This method is referred as random saturation mutagenesis in the disclosure.

In addition, as known to a person skilled in the art, genetic cloning process often requires design of suitable endonuclease sites, which will eventually introduce one or more irrelevant residues to the terminus of the protein to be expressed, but this does not affect the activity of the protein of interest. For another example, in order to construct a fusion protein, to promote the expression of a recombinant protein, to obtain a recombinant protein that is automatically secreted to outside of the host cells, or to facilitate the purification of a recombinant protein, it is often desirable to have the N-terminus, C-terminus, or other suitable regions of the recombinant protein added with some amino acid sequences, for example, including but not limited to linker peptides, signal peptides, leader peptides, terminal extensions, glutathione S-transferase (GST), maltose E binding protein, Protein A, tags such as 6His or Flag, or suitable protease cleavage sites. It should be understood that the presence of these amino acid sequences will not affect the activity of the obtained polypeptide. Therefore, the disclosure also includes a polypeptide having one or more amino acids at the C-terminus and/or N-terminus of the polypeptide of the disclosure or in a suitable region in the protein thereof that facilitate the construction of a vector expressing the polypeptide, the expression and/or purification of the polypeptide. These polypeptides still have the phospholipase C activity described herein.

Therefore, in certain embodiments, the disclosure includes an amino acid sequence having at least 80%, preferably at least 85%, more preferably at least 90%, more preferably at least 95%, more preferably at least 96%, more preferably at least 97%, more preferably at least 98%, more preferably at least 99% sequence identity to SEQ ID NO: 7. Furthermore, the disclosure includes an amino acid sequence having at least 80%, preferably at least 85%, more preferably at least 90%, more preferably at least 95%, more preferably at least 96%, more preferably at least 97%, more preferably at least 98%, more preferably at least 99% sequence identity to SEQ ID NO:4. The amino acid sequences having such sequence identity to SEQ ID NOs:4 and 7 do not have all of the amino acid residues at the positions corresponding to amino acids 6, 8, 10 and 104 of SEQ ID NOs: 4 and 7 mutated; preferably, the amino acid sequences have the same amino acid residues as SEQ ID NOs: 4 and 7 at the positions corresponding to amino acids 6, 8, 10 and 104 of SEQ ID NOs: 4 and 7, for example, have proline, valine, serine and serine at the positions corresponding to amino acids 6, 8, 10 and 104 of SEQ ID NO: 4. More preferably, the amino acid sequence having such sequence identity is obtained from *Bacillus subtilis*. Herein, sequence identity is used to describe the correlation between two amino acid sequences or between two nucleotide sequences. Methods known in the art can be used to calculate sequence identity. For example, the sequence identity between two amino acid sequences can be determined by Needleman-Wunsch algorithm (Needleman and Wunsch, 1970, Journal of Molecular Biology, 48:443-453) implemented in Needle program of the EMBOSS package (EMBOSS: European Molecular Biology Open Software Suite, Rice et al., 2000, Trends in Genetics, 16:276-277). Alternatively, BLAST® protein (also referred to as BLASTP) on NCBI can be used to calculate the sequence identity between two amino acid sequences.

Depending on the host used in the recombinant production, the polypeptide of the disclosure may be glycosylated or non-glycosylated.

Polynucleotide

The disclosure includes a nucleotide sequence encoding the polypeptide of the disclosure or a complementary sequence thereof. SEQ ID NO: 3 shows an example of the coding sequence of the polypeptide of the disclosure. The "coding sequence" includes a nucleic acid sequence encoding the polypeptide of the disclosure (especially SEQ ID NO: 7). The sequence encoding the polypeptide of the disclosure may be identical to for example, the coding region sequence as shown in SEQ ID NO: 3 or a degenerate variant thereof. As used herein, "degenerate variant" in the disclosure refers to a nucleotide sequence that encodes the same amino acid sequence but differs in nucleotide sequence.

The sequence encoding the polypeptide of the disclosure comprises: the coding sequence encoding only the mature polypeptide; the coding sequence of the mature polypeptide and various additional coding sequence; the coding sequence of the mature polypeptide (and optionally additional coding sequence) and a non-coding sequence.

The disclosure also relates to a variant of the above polynucleotides, which encodes fragments, analogs, derivatives and variants of the same amino acid sequence as the disclosure. These nucleotide variants include substitution variants, deletion variants and insertion variants. As known in the art, an allelic variant is an alternate form of a polynucleotide, which may be caused by one or more nucleotide substitutions, deletions or insertions, but does not substantially alter the function of the encoded protein.

The disclosure also includes a fragment of the nucleic acid sequence (such as SEQ ID NO: 3 or its complementary sequence) encoding the polypeptide of the disclosure. As used here, the length of "nucleic acid fragment" contains at least 15 nucleotides, preferably at least 30 nucleotides, more preferably at least 50 nucleotides, and most preferably at least 100 or more nucleotides. The nucleic acid fragment can be used for nucleic acid amplification techniques (e.g. PCR) to determine and/or isolate polynucleotides encoding the polypeptides of the disclosure. Therefore, in some embodiments, the nucleic acid fragment has 15 to 30 bases in length. Known techniques can be used to select appropriate nucleic acid fragments from the nucleic acid sequence of the disclosure, which are used as primers or probes.

Generally, coding sequences of the polypeptides of the disclosure or fragments thereof can be obtained by PCR amplification, recombination or artificially synthetic methods. For PCR amplification, primers can be designed according to a related nucleotide sequence disclosed in the disclosure, particularly an open reading frame sequence. A commercially available cDNA library or a cDNA library prepared using routine methods by person skilled in the art could be used as template for amplifying the related sequence. For longer sequences, two or more individual PCR amplifications are typically desired, which are followed by ligating the separately amplified fragments together in a proper order.

Nucleic Acid Construct

The disclosure also relates to a nucleic acid construct comprising the isolated polynucleotide of the disclosure operably linked to one or more regulatory sequences that direct the coding sequence to be expressed in a suitable host cell under conditions suitable for the regulatory sequences. The term "operably linked" means that the regulatory sequences are located in appropriate positions so as to control and direct the expression of the polynucleotide sequence of interest. The polynucleotide encoding the polypeptide of the disclosure can be manipulated in a variety of ways to ensure the expression of the polypeptide.

The regulatory sequence may be a suitable promoter sequence, a nucleotide sequence recognized by a host cell for expression of a polynucleotide encoding a polypeptide according to the disclosure. The promoter sequence contains transcriptional regulatory sequences that mediate polypeptide expression. The promoter can be any nucleotide sequence having transcriptional activity in the selected host cell, including mutant, truncated, and hybrid promoters, and can be obtained from a gene encoding an extracellular or intracellular polypeptide that is homologous or heterologous to the host cell.

Examples of suitable promoters for directing transcription of the nucleic acid constructs of the disclosure, especially in bacterial host cells, are promoter sequences derived from phage T7 promoter, *E. coli* lac operon, *Streptomyces coelicolor* agarase gene, *Bacillus subtilis* levansucrase gene, *Bacillus licheniformis* alpha-amylase gene, *Bacillus amyloliquefaciens* alpha-amylase gene, *Bacillus licheniformis* penicillinase gene, etc.

Examples of suitable promoters for directing transcription of the nucleic acid construct of the disclosure in filamentous fungal host cells are promoters derived from genes of: *Aspergillus oryzae* TAKA amylase, *Rhizomucor miehei* aspartic protease, *Aspergillus niger* neutral alpha-amylase, *Aspergillus niger* acid stabilized alpha-amylase, *Aspergillus niger* or *Aspergillus awamori* glucoamylase (glaA), *Trichoderma reesei* cellobiohydrolase I, *Trichoderma reesei* cellobiohydrolase II, *Aspergillus oryzae* alkaline protease,

*Aspergillus oryzae* triose phosphate isomerase, *Trichoderma reesei* endoglucanase, etc, or mutated, truncated and hybrid promoters thereof.

In yeast hosts, useful promoters can be obtained from genes of *Saccharomyces cerevisiae* enolase (ENO-1), *Saccharomyces cerevisiae* galactokinase (GAL1), *Saccharomyces cerevisiae* alcohol dehydrogenase, glyceraldehyde 3-phosphate dehydrogenase, *Saccharomyces cerevisiae* triose phosphate isomerase, *Saccharomyces cerevisiae* 3-phosphoglycerate kinase, *Pichia pastoris* alcohol oxidase. Other useful promoters for yeast host cells are described in Romanos et al., 1992, Yeast 8:423-488.

The regulatory sequence may also be a suitable transcription terminator, a sequence recognized by the host cell to terminate transcription. The terminator is operably linked to the 3'end of a nucleotide sequence encoding the polypeptide. Any terminator that is functional in the selected host cell may be used in the disclosure.

A preferred terminator for bacterial hosts may be a terminator from T7 phage.

A preferred terminator for filamentous fungal host cells is obtained from genes of *Aspergillus oryzae* TAKA amylase, *Aspergillus niger* glucoamylase, *Aspergillus nidulans* anthranilate synthase, *Aspergillus niger* alpha-glucosidase.

A preferred terminator for yeast host cells is obtained from genes of *Saccharomyces cerevisiae* enolase, *Saccharomyces cerevisiae* cytochrome C, *Saccharomyces cerevisiae* glyceraldehyde-3-phosphate dehydrogenase, *Pichia pastoris* alcohol oxidase and the like.

The regulatory sequence can also be a suitable leader sequence, an mRNA non-translated-region that is important for translation in host cells. The leader sequence is operably linked to the 5'end of a nucleotide sequence encoding the polypeptide. Any terminator that is functional in the selected host cell may be used in the disclosure.

The regulatory sequence may also be a signal peptide coding region that encodes an amino acid sequence linked to an end of a polypeptide and directs the encoded polypeptide into the cell secretory pathway. The 5' end of the nucleotide coding sequence may inherently contain a signal peptide coding region naturally linked to a translation reading frame containing a segment of the coding region encoding a secreted polypeptide. Alternatively, the 5' end of the coding sequence may contain a signal peptide coding region that is exogenous to the coding region. When the coding sequence does not naturally contain a signal peptide coding region, an exogenous signal peptide coding region may be required. Alternatively, the exogenous signal peptide coding region can simply replace the natural signal peptide coding region to enhance the secretion of the polypeptide. However, any signal peptide coding region that directs the expressed polypeptide into the secretion pathway of the host cell of choice (that is secretion into the culture medium) can be used in the disclosure.

In certain embodiments, the nucleic acid construct of the disclosure is an expression cassette. The term "expression cassette" refers to the complete elements required to express a gene, including promoters, coding sequences, and poly A tailing sequences.

Vector

The disclosure also relates to vectors containing polynucleotides or nucleic acid constructs of the disclosure, including expression vectors and cloning vectors. An expression vector can be any vector (such as a plasmid or virus) that can be conveniently subjected to recombinant DNA methods and can lead to the expression of a nucleotide sequence of interest. A cloning vector is usually capable of multiplying in a host cell after being introduced into the host cell.

The selection of vector generally depends on the compatibility of the vector with the host cell into which the vector is introduced. The vector can be a linear or closed circular plasmid.

The vector may be a self-replicating vector, that is a vector that exists as an extrachromosomal entity whose replication is independent of chromosomal replication, such as a plasmid, an extrachromosomal element, mini-chromosomes or an artificial chromosome. The vector can contain any means to ensure self-replication. Alternatively, the vector may be a vector that, when introduced into a host cell, integrates into the genome and replicates with the chromosome into which it has been integrated. In addition, a single vector or plasmid, or two or more vectors or plasmids, or transposon(s) can be used, which together contain the total DNA to be introduced into the genome of the host cell.

The vector of the disclosure preferably contains one or more selectable markers that allow easy selection of transformed, transfected, transduced cells and the like. Selectable markers are genes whose products provide resistance to antibiotics or viruses, resistance to heavy metals, prototrophy to auxotrophy, etc.

The vector of the disclosure preferably contains elements that allow the vector to be integrated into the genome of the host cell or that allow the vector to be self-replicated in cells independently of the genome.

More than one copy of the polynucleotides of the disclosure can be inserted into a host cell to increase the yield of the gene product. Multiple copy of the polynucleotides can be obtained by integrating at least one additional copy of the sequence into the host cell genome or by including the polynucleotide and a selectable marker gene that is amplifiable. Cells containing an amplified copy of the selectable marker gene and thereby containing the additional copy of the polynucleotide can be selected by culturing the cell in the presence of an appropriate selection agent.

The vector of the disclosure preferably contains an artificially synthetic sequence containing multiple restriction-endonuclease-recognition sites, which can provide a variety of insertion positions or insertion schemes for exogenous DNAs.

The expression vector of the disclosure is more preferably a vector that can be used for expression in *Pichia pastoris*. The vector of the disclosure is preferably one used in commercial *Pichia pastoris*, such as pPIC, pPICZ, pAO, pGAP or pGAPZ or a vector of the same series.

Host Cell

The disclosure also relates to a recombinant host cell containing the polynucleotide or nucleic acid construct of the disclosure that is used for recombinant production of polypeptides. A vector comprising a polynucleotide according to the disclosure is introduced into a host cell so that the vector is maintained as a part of the chromosome or as an extrachromosomal self-replicating vector as described earlier. The selection of a host cell largely depends on the polypeptide encoding gene and its source.

The host cell may be a unicellular microorganism or a non-unicellular microorganism. Unicellular microorganisms such as gram positive bacteria include but are not limited to a *Bacillus* cell, e.g., *Bacillus alkalophilus, Bacillus amyloliquefaciens, Bacillus brevis, Bacillus megaterium, Bacillus subtilis Bacillus licheniformis Bacillus coagulans, Bacillus stearothermophilus, Bacillus thuringiensis* and the like; or a *Streptomyces* cell, e.g., *Streptomyces lividans*; or gram negative bacteria such as *E. coli* and *Pseudomonas* sp. In a preferred aspect, the bacterial host is *Bacillus subtilis, E. coli, Bacillus licheniformis, Bacillus stearothermophilus* and *E. coli* cells.

The host cell may be a eukaryote, such as a mammalian, insect, plant, yeast or fungal cell. In a preferred aspect, the host cell is a eukaryotic cell. As used herein, "eukaryotic" includes Ascomycota, Basidiomycota, Chytridiomycota, Zygomycota, Oomycota and the like.

In a more preferred aspect, the host cell is a cell of Ascomycota such as *Saccharomyces* sp., *Pichia* sp., *Yarrowia* sp., *Candida* sp. and *Komagataella* sp.

In a most preferred aspect, the host cell is *Pichia pastoris Saccharomyces cerevisiae, Yarrowia lipolytica* and the like. In another most preferred aspect, the host cell is a *Pichia pastoris* cell.

Production Method

After obtaining the coding sequence of a polypeptide, a method may be employed for producing a polypeptide according to the disclosure, the method comprising: (a) culturing a host cell containing an expression vector of the polypeptide under conditions conducive to production of the polypeptide; and (b) recovering the polypeptide.

In production method according to the disclosure, the cells may be cultured in a medium suitable for the production of the polypeptide using methods known in the art. For example, the cells can be subjected to the shake flask culture in laboratory or industrial fermentors and small-scale or large-scale fermentation (including continuous, batch, feed-batch, or solid state fermentations), and cultured in a suitable medium and conditions allowing expression and/or separation of the polypeptide. The cultivation takes place in a suitable media comprising carbon and nitrogen sources and inorganic salts using methods known in the art. A suitable media may be obtained from a commercial supplier or may be prepared according to a published composition. If the polypeptide is secreted into the medium, the polypeptide can be recovered directly from the medium. If the polypeptide is not secreted into the medium, it can be recovered from cell lysates.

Alternatively, a polypeptide according to the disclosure may also be synthesized with a chemical synthesis method known in the art. Chemical synthesis methods for a polypeptide include solid phase synthesis and liquid phase synthesis method, wherein the solid phase synthesis is commonly used. Solid phase synthesis methods include, but are not limited to two common methods, Fmoc and tBoc. Typically, resin is used as an insoluble solid support, amino acids are typically connected one by one from the C-terminus (carboxy terminus) to the N-terminus (amino terminus) onto the peptide chain, and each amino acid linkage cycle consists of the following three steps: 1) deprotection: in a protected amino acid, the protecting group of the amino acid must be removed using a de-protecting solvent; 2) activation: the carboxyl group of the amino acid to be connected is activated by an activator; and 3) coupling: the activated carboxyl is reacted with the exposed amino group of the previous amino acid to form a peptide bond. The cycle is repeated until the peptide chain is extended to a desirable length. Finally, the connection between the solid support and the peptide chain is cleaved by cleaving solution, and the desired amino acid sequence can be obtained. Above chemical synthesis could be conducted on a program-controlled automated peptide synthesizer, and such instruments include but are not limited to Tribute dual-channel peptide synthesizer from Protein Technologies, UV Online Monitor System from CS Bio Company, Focus XC three channel synthesizer from Aapptec and the like.

The polypeptide described herein may be recovered with a method known in the art. For example, a polypeptide may be recycled from the media by conventional methods, including but not limited to centrifugation, filtration, ultrafiltration, extraction, chromatography, spray drying, freeze drying, evaporation, precipitation or the like.

A polypeptide according to the disclosure can be purified by a variety of methods known in the art, including but not limited to chromatography (e.g., ion exchange, affinity, hydrophobic, chromatofocusing, size exclusion), electrophoresis (e.g., isoelectric focusing), differential solubility (such as salting-out precipitation), SDS-PAGE, or extraction method to obtain a substantially pure polypeptide.

Properties and Uses of the Polypeptide

A polypeptide according to the disclosure has phospholipase C activity, which may be used for oil and fat refining, phospholipid modification, feed modifier and various aspects in food industry and pharmaceutical industry, including but not limited to baking, detergents, improvement of filtration of aqueous or syrup and the like. When used for degumming, the polypeptide of the disclosure can improve the degumming efficiency and increase the yield of DAG during the degumming process.

A polypeptide according to the disclosure may be provided in form of pure enzyme preparation, or in form of a composition. The composition may be a powdered composition, a liquid composition, or a pasty composition. When provided in the form of composition, the composition may contain various excipients according to the different uses of the enzyme-containing composition. Excipients known in the art may be added to the compositions according to the disclosure, and such excipients include but are not limited to sorbitol, potassium sorbate, methyl benzoate, ethyl benzoate, sucrose, mannitol, trehalose, starch, sodium chloride, calcium chloride, other stabilizers or one or more other substances.

The amount of the polypeptide according to the disclosure used in the method according to the disclosure can be practically determined.

Enzymatic Degumming

The disclosure also provides a method for enzymatic degumming, comprising adding a polypeptide according to the disclosure to crude oil for degumming. Typically, the crude oil is heated to 50 to 70° C., preferably 50 to 60° C., and then added with a polypeptide according to the disclosure, namely phospholipase C.

The phospholipase C according to the disclosure is normally added as aqueous solution. Based on the weight of crude oil, the enzyme is added in an amount of 10 to 1000 ppm, preferably 50 to 500 ppm, more preferably 100 to 300 ppm.

Degumming conditions typically includes: stirring at 50 to 60° C. for 1 to 3 hours, and then heating to 80 to 90° C. and holding for 1 to 10 minutes.

Crude oil suitable for the degumming process of the disclosure include, but are not limited to soybean oil, sunflower oil, peanut oil, rapeseed oil, rice bran oil, corn oil, olive oil, palm oil, palm kernel oil, palm olein, canola oil, castor oil, coconut oil, coriander oil, cottonseed oil, hazelnut oil, hempseed oil, linseed oil, mango kernel oil, meadowfoam oil, neat's foot oil, safflower oil, camellia oil, tall oil, tsubaki oil and other vegetable oils.

The present disclosure will be illustrated by way of specific examples below. Experimental methods with no specific conditions specified in the examples below, are performed under routine conditions, such as those in Sambrook et al., "Molecular Cloning: A Laboratory Manual" (New York: Cold Spring Harbor Laboratory Press (Cold Spring Harbor Laboratory Press), 1989), or the conditions recommended by the manufacturer. Usage and dosage of reagents, unless otherwise specified, are in accordance with conventional usage and dosage.

Experimental Materials

1. Experimental Strains and Plasmids

Strains: Pichia pastoris SMD1168 (Invitrogen, Catalog No. C17500), E. coli DH5a (TAKARA, Catalog No. D9057A).

2. Media and Solutions

LB liquid medium: 0.5% yeast extract, 1% tryptone, 1% NaCl, pH 7.0.

LB solid medium: 1.5% agar added to the LB liquid medium.

YPD liquid medium: 1% yeast extract, 2% peptone, 2% glucose.

YPD solid medium: 2% agar added to the LB liquid medium.

MGYS solid medium: 1.34% yeast nitrogen base (YNB) containing ammonium sulfate without amino acids, 1% glycerol, 1M sorbitol, $4\times10^{-5}$% D-biotin, 2% agar.

BMM-soybean phospholipid screening medium: 1.34% yeast nitrogen base (YNB) containing ammonium sulfate without amino acids, 4× 10-5% D-biotin, 0.5% methanol (sterilized), 2% soybean phospholipid emulsion, 0.1M citric acid-sodium citrate buffer at pH 6.6, 2% agar, 10 uM $ZnSO_4 \cdot 7H_2O$.

2% Soybean phospholipid emulsion: 2 g soybean phospholipid, 100 ml $H_2O$, homogenized with high speed homogenizer at 8000 rpm for 1 min.

BMGY liquid medium: 1% yeast extract, 2% peptone, 1.34% yeast nitrogen base (YNB) containing ammonium sulfate without amino acids, 1% glycerin, $4\times10^{-5}$% D-biotin, 0.1M potassium dihydrogen phosphate-dipotassium hydrogen phosphate buffer at pH 6.0.

BMMY liquid medium: 1% yeast extract, 2% peptone, 1.34% yeast nitrogen base (YNB) containing ammonium sulfate without amino acids, 0.3% $ZnSO_4 \cdot 7H_2O$, 0.5% methanol (sterilized), $4\times10^{-5}$% D-Biotin (sterilized), 0.1M citric acid-sodium citrate buffer at pH 6.6.

3. Determination of Enzyme Activity by pNPPC Method

Plotting of Standard Curve for Determination of Phospholipase Activity:

0.01391 g of p-nitrophenol was dissolved in 50 ml of sterile water to obtain a 2 mmol/L working solution. The amount of each reagent is shown in the table below. The reaction volume and reaction conditions for the standard curve are consistent with the conditions for measuring the enzyme activity of the sample in the experiment.

| No. | 1 | 2 | 3 | 4 | 5 | 6 | 7 |
|---|---|---|---|---|---|---|---|
| 2.0 mmol/L pNP(ul) | 0 | 7.5 | 15 | 22.5 | 30 | 37.5 | 45 |
| ddH$_2$O (ul) | 62.5 | 55 | 47.5 | 40 | 32.5 | 25 | 17.5 |
| Substrate Buffer (ml) | 562.5 | 562.5 | 562.5 | 562.5 | 562.5 | 562.5 | 562.5 |
| Total pNP (umol) | 0 | 0.06 | 0.12 | 0.18 | 0.24 | 0.30 | 0.36 |

Figure 3:
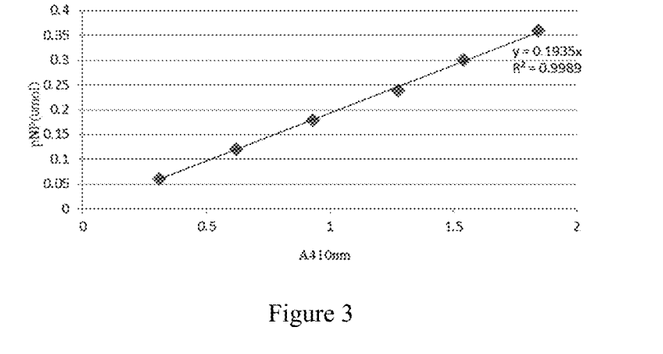
FIG. 3: Standard curve for determination of phospholipase activity.

The above solutions were mixed and treated at 37° C. for 15 minutes. 500 ul 0.5N NaOH was added and the absorbance at 410 nm was measured. The resulting standard curve is shown in FIG. 3.

4. Reaction Buffer 0.1M boric acid-sodium borate buffer (pH 7.6), 20 mM pNPPC.

5. Calculation of Enzyme Activity 25 ul of the enzyme solution to be tested was added to 600 ul of the above reaction buffer and reacted at 37° C. for 15 min. 500 ul 0.5N NaOH was added to stop the reaction, and the absorbance at 410 nm was measured.

Sample enzyme activity (U/ml)=$A$(absorbance at 410 nm)*0.1935*dilution fold*10/15

The advanced Bradford protein concentration kit was available from Shanghai Sangon Biotech Co., Ltd.; PCR enzyme PrimeSTAR® HS DNA Polymerase was available from TaKaRa (Dalian) Co., Ltd; T4 DNA ligase was available from Fermentas Co., Ltd.

Example 1: Construction and Screening of Saturation Mutant Library

A random saturation mutation library for the amino acids 6, 8, 10, 104, and 205 were constructed by Synbio Technologies (Suzhou) Co., Ltd. using the pmAO-PLC-N63DN131SN134D-Y56H vector (CN 201680072289.5, the DNA sequence of PLC-N63DN131SN134D-Y56H is shown in SEQ ID NO: 1, and its amino acid sequence is shown in SEQ ID NO: 2) as a template. The plasmid library was transformed into E. coli DH5α strain, and all E. coli clones were washed into LB liquid medium (containing 100 µg/ml ampicillin), and cultured at 37° C. for 4 hours. The plasmid was extracted and linearized by SalI, and a fragment of about 8.5 kb was recovered. 500 ng of vector was transformed into competent cells of Pichia pastoris SMD1168 by electro-transformation. The transformants were inoculated on MGYS plates and cultured at 30° C. for 3 days to obtain a library of PLC-N63DN131SN134D-Y56H Pichia pastoris mutants. Monoclonal strains were selected and transferred from the plate to a BMM-soybean phospholipid screening plate. One of the clones with a relatively large white precipitation circle was selected and numbered as 31 #.

Example 2: Sequence Analysis of 31# Mutant

The 31# strain was inoculated in 3 ml YPD liquid medium and cultured overnight at 30° C., then from which genomic DNAs were extracted. DNA sequence of the PLC in the 31# strain was amplified by PCR using PrimeSTAR® HS DNA polymerase, primer pair AOX1-5/AOX1-3, and the genomic DNAs of the 31# strain as templates. The obtained sequence was sequenced by Shanghai Sangon Biotech Co., Ltd., using primer pair AOX1-5/AOX1-3.

AOX1-5: CGACTGGTTCCAATTGACAACG (SEQ ID NO: 5);

AOX1-3: GGCAAATGGCATTCTGACATCCTC (SEQ ID NO: 6).

The DNA sequencing result of 31# PLC is shown in SEQ ID NO: 3. According to the result, 5 bases of the DNA sequence of 31# PLC are mutated. The amino acid sequence is shown in SEQ ID NO: 4, wherein the amino acids at positions 6, 8, 10 and 104 were mutated from lysine, lysine, glycine and lysine to proline, valine, serine and serine, respectively.

Example 3: Shake Flask Fermentation of 31# Mutant and Detection of Enzymatic Activity Thereof 31# Strains and the original strains (i.e., SMD1168 transferred with pmAO-PLC-N63DN131SN134D-Y56H vector) were activated in liquid YPD, and then inoculated into BMGY medium and subjected to 220 rpm shaking at 30° C. overnight. The culture was transferred to BMMY medium with an initial OD600 of 6.

First, induction was performed with 2% methanol, supplemented with 1% methanol after 24 h, 32 h, 48 h and 56 h, respectively, and sampled at 72 h. The obtained samples were concentrated by 40-fold by ultrafiltration desalting with ultrafiltration tubes having a molecular weight cut-off of 40 kDa. The treated samples were added to a buffer (20 mM citric acid-sodium citrate buffer (pH 6.6), 10 uM $ZnSO_4$).

Figure 1:
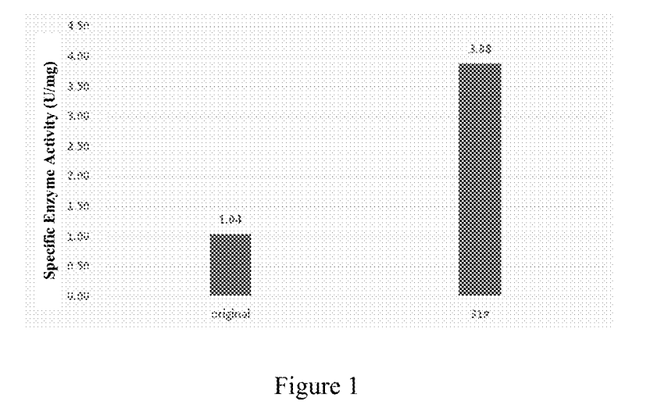
FIG. 1: Specific enzyme activity of mutants.

0.5 µl of fermentation broth concentrate was added to 600 ul pNPPC reaction buffer and reacted at 37° C. for 15 min. 500 ul 0.5N NaOH was added to stop the reaction, and the absorbance at 410 nm was measured. According to the standard curve, the PLC activity of each fermentation broth sample was calculated. The protein concentration in the fermentation broth in the shaken flask was detected with Bradford reagent to obtain the specific enzyme activity. The results are shown in FIG. 1. The specific enzyme activity of the fermentation broth sample of 31# mutant is 1.88 times higher than that of the fermentation broth sample of the original strain.

Figure 2:
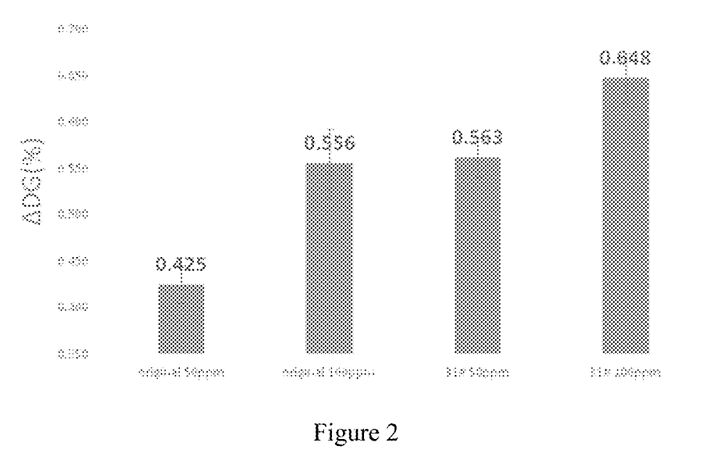
FIG. 2: The results of the small-scale degumming test.

Example 4: 31# Degumming Test 100 g of soybean crude oil was heated to 55° C., and added with 50 ppm and 100 ppm fermentation broth sample of 31# mutant and the original strain obtained in Example 3, respectively. The water phase in the obtained system was 3%. The system was high-speed sheared (10000 r/min) for 1 min by a high-speed shearing machine, stirred (750 r/min) at 55° C. for 2 h, heated to 85° C. and held for 5 min, and centrifuged at 12000 rpm for 10 min. About 10 g upper oil sample was used to detect DAG content by HPLC. The DAG increase over crude oil of 31# mutant fermentation broth sample and the original strain fermentation broth sample is shown in FIG. 2. The DAG increase of 31# mutant fermentation broth sample at 50 ppm of enzyme and the original strain fermentation broth sample at 100 ppm of enzyme is the same. Therefore, the required enzyme amount of 31# mutant fermentation broth sample can be reduced by 1 fold as compared with the fermentation broth sample of the original strain.

We claim:

1. An isolated polypeptide having at least 95% sequence identity to SEQ ID NO:4, wherein the amino acid residues of the isolated polypeptide that correspond to amino acids 6, 8, 10 and 104 of SEQ ID NO: 4 are proline, valine, serine and serine, respectively.

2. A polynucleotide selected from the group consisting of:
   (1) a polynucleotide encoding the polypeptide according to claim 1; and
   (2) the complement of the polynucleotide of (1).

3. A nucleic acid construct, comprising the polynucleotide according to claim 2 and one or more regulatory sequences operably linked to the polynucleotide.

4. A genetically engineered host cell, comprising the polynucleotide according to claim 2 or a nucleic acid construct comprising the polynucleotide according to claim 2.

5. A composition comprising the polypeptide according to claim 1 and adjuvants.

6. An enzymatic degumming method, comprising a step of contacting the polypeptide according to claim 1 with crude oil.

7. The method according to claim 6, wherein the method comprises one or more of the following features:
   (1) the polypeptide is added in an amount of 10 to 1000 ppm, based on the weight of the crude oil;
   (2) the degumming includes: stirring at 50 to 60° C. for 1 to 3 hours, and then raising the temperature to 80 to 90° C. and holding for 1 to 10 minutes; and
   (3) the crude oil is selected from the group consisting of: soybean oil, sunflower oil, peanut oil, rapeseed oil, rice bran oil, corn oil, olive oil, palm oil, palm kernel oil, palm olein, canola oil, castor oil, coconut oil, coriander oil, cottonseed oil, hazelnut oil, hempseed oil, linseed oil, mango kernel oil, meadowfoam oil, neat's foot oil, safflower oil, camellia oil, tall oil, and tsubaki oil.

8. The isolated polypeptide according to claim 1, wherein the isolated polypeptide is as shown in SEQ ID NO: 4.

9. The isolated polypeptide according to claim 1, wherein the polypeptide is obtained from *Bacillus subtilis*.

10. The polynucleotide according to claim 2, wherein the polynucleotide is as shown in SEQ ID NO: 3.

11. The nucleic acid construct according to claim 3, wherein the nucleic acid construct is an expression vector or a cloning vector.

12. The composition according to claim 5, wherein the adjuvants are adsorption materials selected from the group consisting of: activated carbon, alumina, diatomaceous earth, porous ceramics, and porous glass.

13. The composition according to claim 5, wherein the polypeptide is as shown in SEQ ID NO: 4.

14. The method according to claim 6, wherein the step includes contacting the polypeptide with a crude oil at a temperature of 50 to 70° C.

15. The method according to claim 6, wherein the polypeptide is as shown in SEQ ID NO: 4.

16. The method according to claim 7, wherein the polypeptide is added in an amount of 50 to 500 ppm, based on the weight of the crude oil.

17. The method according to claim 7, wherein the polypeptide is added in an amount of 100 to 300 ppm, based on the weight of the crude oil.

* * * * *